United States Patent
Fertala et al.

(10) Patent No.: US 6,753,311 B2
(45) Date of Patent: Jun. 22, 2004

(54) COLLAGEN OR COLLAGEN-LIKE PEPTIDE CONTAINING POLYMERIC MATRICES

(75) Inventors: Andrzej Fertala, Voorhees, NJ (US); Frank Ko, Philadelphia, PA (US)

(73) Assignee: Drexel University, Phiadelphia, PA (US)

( * ) Notice: Subject to any disclaimer, the term of this patent is extended or adjusted under 35 U.S.C. 154(b) by 0 days.

(21) Appl. No.: 09/895,674

(22) Filed: Jun. 28, 2001

(65) Prior Publication Data

US 2003/0021821 A1 Jan. 30, 2003

Related U.S. Application Data

(63) Continuation-in-part of application No. PCT/US01/41133, filed on Jun. 25, 2001.
(60) Provisional application No. 60/214,034, filed on Jun. 23, 2000.

(51) Int. Cl.[7] .............................................. A61K 38/39
(52) U.S. Cl. .............................................. 514/2; 514/21
(58) Field of Search ....................................... 514/2, 21

(56) References Cited

U.S. PATENT DOCUMENTS

| | | |
|---|---|---|
| 1,975,504 A | 10/1934 | Formhals |
| 3,991,766 A | 11/1976 | Schmitt et al. .......... 128/335.5 |
| 4,655,777 A | 4/1987 | Dunn et al. .................... 623/16 |
| 4,818,542 A | 4/1989 | DeLuca et al. ............. 424/491 |
| 5,128,170 A | 7/1992 | Matsuda et al. ................ 427/2 |
| 5,545,409 A | 8/1996 | Laurencin et al. .......... 424/426 |
| 5,759,830 A * | 6/1998 | Vacanti et al. .............. 435/180 |
| 5,769,830 A | 6/1998 | Parker ........................ 604/282 |
| 5,969,020 A | 10/1999 | Shalaby et al. ............. 524/167 |

FOREIGN PATENT DOCUMENTS

| | | | |
|---|---|---|---|
| WO | WO 99/18893 | 4/1999 | |
| WO | WO 0023008 | * 4/2000 | ............. A61F/2/24 |

OTHER PUBLICATIONS

Doshi, J. and Reneker, D.H., "Electrospinning Process and Applications of Electrospun Fibers", *Journal of Electrostatics* 1995 35:151–160.
Gibson et al., "Electrospun Fiber Mats:Transport Properties", *AIChE Journal* 1999 45:190–195.
Ko et al., "The Dynaimcs of Cell–Fiber Architecture Interaction," *Proceedings, Annual Meeting, Biomaterials Research Society*, San Diego, CA, Apr. 1998.
Reneker, D.H. and Chun, I., "Nanometre diameter fibres of polymer, produced by electrospinning", *Nanotechnology* 1996 7:216–223.

* cited by examiner

*Primary Examiner*—Jean C. Witz
(74) *Attorney, Agent, or Firm*—Licata & Tyrrell P.C.

(57) ABSTRACT

Tissue engineering scaffolds comprising collagen or a collagen-like peptides incorporated within or between polymeric fibers and methods for their production are provided.

4 Claims, No Drawings

SEQUENCE LISTING

<160> NUMBER OF SEQ ID NOS: 1

<210> SEQ ID NO 1
<211> LENGTH: 234
<212> TYPE: PRT
<213> ORGANISM: Homo sapiens

<400> SEQUENCE: 1

```
Gly Arg Val Gly Pro Pro Gly Ser Asn Gly Asn Pro Gly Pro Pro Gly
  1               5                  10                  15

Pro Pro Gly Pro Ser Gly Lys Asp Gly Pro Lys Gly Ala Arg Gly Asp
             20                  25                  30

Ser Gly Pro Pro Gly Arg Ala Gly Glu Pro Gly Leu Gln Gly Pro Ala
         35                  40                  45

Gly Pro Pro Gly Glu Lys Gly Glu Pro Gly Asp Asp Gly Pro Ser Gly
     50                  55                  60

Ala Glu Gly Pro Pro Gly Pro Gln Gly Leu Ala Gly Gln Arg Gly Ile
 65                  70                  75                  80

Val Gly Leu Pro Gly Gln Arg Gly Glu Arg Gly Phe Pro Gly Leu Pro
                 85                  90                  95

Gly Pro Ser Gly Glu Pro Gly Gln Gln Gly Ala Pro Gly Ala Ser Gly
            100                 105                 110

Asp Arg Gly Pro Pro Gly Pro Val Gly Pro Pro Gly Leu Thr Gly Pro
        115                 120                 125

Ala Gly Glu Pro Gly Arg Glu Gly Ser Pro Gly Ala Asp Gly Pro Pro
    130                 135                 140

Gly Arg Asp Gly Ala Ala Gly Val Lys Gly Asp Arg Gly Glu Thr Gly
145                 150                 155                 160
```

-continued

```
Ala Val Gly Ala Pro Gly Ala Pro Gly Pro Pro Gly Ser Pro Gly Pro
            165             170                 175

Ala Gly Pro Thr Gly Lys Gln Gly Asp Arg Gly Glu Ala Gly Ala Gln
            180             185                 190

Gly Pro Met Gly Pro Ser Gly Pro Ala Gly Ala Arg Gly Ile Gln Gly
        195             200             205

Pro Gln Gly Pro Arg Gly Asp Lys Gly Glu Ala Gly Glu Pro Gly Glu
    210             215             220

Arg Gly Leu Lys Gly His Arg Gly Phe Thr
225             230
```

COLLAGEN OR COLLAGEN-LIKE PEPTIDE CONTAINING POLYMERIC MATRICES

INTRODUCTION

This application is a continuation-in-part of PCT Application No. PCT/US01/41133, filed Jun. 25, 2001, which claims the benefit of priority from U.S. Provisional Application Serial No. 60/214,034, filed Jun. 23, 2000.

FIELD OF THE INVENTION

The present invention relates to polymeric fiber matrices, film coatings or braided/woven structures for the controlled release of bioactive compounds. The delivery systems of the present invention may be comprised of either biodegradable or nondegrading polymeric fibers. In one embodiment, these fibers have submicron and/or micron diameters. Bioactive compounds are included in the delivery system either by suspending the compound particles or dissolving the compound in the polymer solution used to produce the fibers. In one embodiment of the present invention, the polymeric matrix is used as a tissue engineering scaffold and the bioactive compound of the polymeric matrix comprises collagen or a collagen-like polypeptide incorporated within or between the polymeric fibers. This tissue engineering scaffold is particularly useful in promoting attachment and growth of chondrocytes and thus is useful in cartilage repair and replacement.

BACKGROUND OF THE INVENTION

A number of polymer matrices for use in the controlled release and/or delivery of bioactive compounds, and for particular drugs, have been described.

U.S. Pat. No. 3,991,766 describes a medicament repository consisting of a surgical element in the form of tubes, sheets, sponges, gauzes or prosthetic devices of polyglycolic acid having incorporated therein an effective amount of a medicament.

U.S. Pat. No. 4,655,777 describes a method for producing a biodegradable prothesis or implant by encasing an effective amount of fibers of calcium phosphate or calcium aluminate in a matrix of polymer selected from the group consisting of polyglycolide, poly(DL-lactide), poly(L-lactide), polycaprolactone, polydioxanone, polyesteramides, copolyoxalates, polycarbonates, poly(glutamic-co-leucine) and blends, copolymers and terpolymers thereof to form a composite.

U.S. Pat. No. 4,818,542 discloses a method for preparing a spherical microporous polymeric network with interconnecting channels having a drug distributed within the channels.

U.S. Pat. No. 5,128,170 discloses a medical device and methods for manufacturing medical devices with a highly biocompatible surface wherein hydrophillic polymer is bonded onto the surface of the medical device covalently through a nitrogen atom.

U.S. Pat. No. 5,545,409 discloses a composition and method for controlled release of water-soluble proteins comprising a surface-eroding polymer matrix and water-soluble bioactive growth factors.

U.S. Pat. No. 5,898,040 discloses a polymeric article for use in drug delivery systems which comprises a polymeric substrate with a highly uniform microporous polymeric surface layer on at least part of the substrate.

Encapsulation of a bioactive compound within a polymer matrix has also been described. For example, WO 93/07861 discloses polymer microspheres of 50 to 100 microns comprising a compound contained in a fixed oil within the polymer microsphere. U.S. Pat. No. 5,969,020 discloses a foam precursor comprising a crystalline thermoplastic polymer and solid crystalline additive for use in preparation of drug delivery systems.

Recently, it has been shown that polymer fibers of nanometer diameter can be electrospun from sulfuric acid into a coagulation bath (Reneker, D. H. and Chun, I. Nanotechnology 1996 7:216). In these studies more than 20 polymers including polyethylene oxide, nylon, polyimide, DNA, polyaramide and polyaniline were electrospun into electrically charged fibers which were then collected in sheets or other useful geometrical forms. Electrospinning techniques have also been applied to the production of high performance filters (Doshi, J. and Reneker, D. H. Journal of Electrostatics 1995 35:151; Gibson et al. AIChE Journal 1999 45:190) and for scaffolds in tissue engineering (Doshi, J. and Reneker, D. H. Journal of Electrostatics 1995 35:151; Ko et al. "The Dynamics of Cell-Fiber Architecture Interaction," Proceedings, Annual Meeting, Biomaterials Research Society, San Diego, Calif., Apr. 1998; and WO 99/18893).

A number of polymer matrices for use as tissue engineering scaffolds have been described.

WO 99/18893 describes a method for preparing nanofibrils from both nondegrading and biodegradable polymers for use as tissue engineering scaffolds.

U.S. Pat. No. 5,769,830 discloses synthetic, biocompatible, biodegradable polymer fiber scaffolds for cell growth. Fibers are spaced apart by a distance of about 100 to 300 microns for diffusion and may comprise polyanhydrides, polyorthoesters, polyglycolic acid or polymethacrylate. The scaffolds may be coated withe materials such as agar, agarons, gelatin, gum arabic, basement membrane material, collagen type I, II, III, IV or V, fibronectin, laminin, glycosaminoglycans, and mixtures thereof.

The present invention relates to delivery systems for the controlled release of bioactive compounds which comprise polymeric fibers, and the bioactive compound. In one embodiment, the system of the present invention is used as a tissue engineering scaffold wherein the bioactive compound comprises collagen or a collagen-like peptide.

SUMMARY OF THE INVENTION

An object of the present invention is to provide a system for delivery of bioactive compounds comprising a bioactive compound incorporated within or between a polymeric fiber matrix or linear assembly, film coating or braided/woven structure. In one embodiment of the present invention, the system is used as a tissue engineering scaffold and the bioactive compound incorporated within or between a polymeric fiber matrix comprises collagen or a collagen-like peptide. These tissue engineering scaffolds are particularly useful in cartilage repair or replacement as they promote the attachment, growth and spreading of chondrocytes.

DETAILED DESCRIPTION OF THE INVENTION

Electrospinning is a simple and low cost electrostatic self-assembly method capable of fabricating a large variety of long, meter-length, organic polymer fibers with micron or submicron diameters, in linear, 2-D and 3-D architecture. Electrospinning techniques have been available since the 1930's (U.S. Pat. No. 1,975,504). In the electrospinning process, a high voltage electric field is generated between oppositely charged polymer fluid contained in a glass syringe with a capillary tip and a metallic collection screen. As the voltage is increased, the charged polymer solution is attracted to the screen. Once the voltage reaches a critical value, the charge overcomes the surface tension of the suspended polymer cone formed on the capillary tip of the syringe and a jet of ultrafine fibers is produced. As the charged fibers are splayed, the solvent quickly evaporates and the fibers are accumulated randomly on the surface of the collection screen. This results in a nonwoven mesh of nano and micron scale fibers. Varying the charge density (applied voltage), polymer solution concentration, solvent used, and the duration of electrospinning can control the fiber diameter and mesh thickness. Other electrospinning parameters which may be varied routinely to effect the fiber matrix properties include distance between the needle and collection plate, the angle of syringe with respect to the collection plate, and the applied voltage.

In the present invention, electrospinning is used to produce polymeric fiber matrices with the capability of releasing bioactive compounds in a controlled manner over a selected period of time. In one embodiment, the delivery system of the present invention is used to maintain delivery of a steady concentration of bioactive compound. In another embodiment, the delivery system is used in pulsed delivery of the bioactive compound wherein the compound is released in multiple phases in accordance with either rapid or slow degradation of the polymer fibers or diffusion of the bioactive compound from the polymer fibers. In yet another embodiment, the delivery system is used to obtain a delayed release of a bioactive compound. For example, the bioactive compound-containing fiber polymer matrix can be coated with a layer of nonwoven polymer fiber matrix with no bioactive compound. In this embodiment, different polymers with different degradation times can be used to obtain the desired time delays.

The delivery systems of the present invention can be used to deliver a single bioactive compound, more than one bioactive compound at the same time, or more than one bioactive compound in sequence. Thus, as used herein, the phrases "a bioactive compound" and "the bioactive compound", are meant to be inclusive of one or more bioactive compounds.

For purposes of the present invention by "fiber" it is meant to include fibrils ranging in diameter from submicron, i.e. approximately 1 to 100 nanometers ($10^{-9}$ to $10^{-7}$ meters) to micron, i.e. approximately 1–1000 micrometers. The bioactive compound is incorporated within the polymeric fibers either by suspension of compound particles or dissolution of the compound in the solvent used to dissolve the polymer prior to electrospinning of the polymeric fibers. For purposes of the present invention, by "incorporated within" it is meant to include embodiments wherein the bioactive compound is inside the fiber as well as embodiments wherein the bioactive compound is dispersed between the fibers. The polymeric fibers comprising the bioactive compound can be arranged as matrices, linear assemblies, or braided or woven structures. In addition, the fibers which release a bioactive compound can serve as film coatings for devices such as implants, tissue engineering scaffolds, pumps, pacemakers and other composites. Alternatively, the polymeric fiber matrix may be incorporated with a bioactive compound which promotes cell adhesion and growth and serve itself as the tissue engineering scaffold.

These fiber assemblies can be spun from any polymer which can be dissolved in a solvent. The solvent can be either organic or aqueous depending upon the selected polymer. Examples of polymers which can be used in production of the polymeric fibers of the present invention include, but are not limited to, nondegradable polymers such as polyethylenes, polyurethanes, and EVA, and biodegradable polymers such as poly(lactic acid-glycolic acid), poly (lactic acid), poly(glycolic acid), poly(glaxanone), poly (orthoesters), poly(pyrolic acid) and poly(phosphazenes).

Examples of bioactive compounds which can be incorporated into the polymeric fibers include any drug for which controlled release in a patient is desired. Some examples include, but are not limited to, steroids, antifungal agents, and anticancer agents. Other bioactive compounds of particular use in the present invention include tissue growth factors, angiogenesis factors, and anti-clotting factors.

For polymeric fiber matrices of the present invention used as tissue engineering scaffolds, a preferred bioactive compound to be incorporated into the matrix is collagen, preferably collagen II, or a collagen-like peptides. In a preferred embodiment, a collagen-like peptide comprising amino acids 703 to 936 (SEQ ID NO:1) of collagen II, also referred to as the D4 period of collagen II is incorporated into the matrix. Spreading and migration assays have shown the D4 period, which is between residues 703 to 936 (SEQ ID NO:1), to contain amino acids critical for cell motility.

If the bioactive compound is to reside within or inside the polymer fiber, selection of the polymer should be based upon the solubility of the bioactive compound within the polymer solution. Water soluble polymers such as polyethylene oxide can be used if the bioactive compound also dissolves in water. Alternatively, hydrophobic bioactive compounds which are soluble in organic solvent such as steroids can be dissolved in an organic solvent together with a hydrophobic polymer such as polylactic glycolic acid (PLAGA).

If the bioactive compound is to reside between the polymer fibers, dissolution of the bioactive compound in the polymer solution is not required. Instead, the bioactive compound can be suspended in the polymer solution prior to electrospinning of the fibers.

In one embodiment of the present invention, the bioactive compound-containing fibers can be splayed directly onto devices such as implants, tissue engineering scaffolds, pumps and pacemakers as a film coating. For implants and tissue engineering scaffolds, examples of preferred bioactive compounds include tissue growth factors and angiogenesis factors. For pumps or pacemakers, the bioactive compound may comprise an anti-clotting factor. The coated device is then implanted into a patient wherein the bioactive compound or compounds are released upon degradation of or by diffusion from, or combinations thereof, the polymeric fiber film.

In another embodiment, a matrix or linear assembly of the bioactive compound-containing fibers is prepared. In this embodiment, the matrix or linear assembly of bioactive compound-containing fibers can be sandwiched between layers of polymer which contain no bioactive compound to decrease any burst effect and/or to obtain a delayed release. Alternatively, the matrix may comprise layers of fibers containing different bioactive compounds. The matrix or linear assembly is then implanted into a patient for controlled release of the bioactive compound as the polymeric fibers degrade or as the bioactive compound diffuses from the polymeric fibers. The time delay can be controlled by varying the choice of polymer used in the fibers, the concentration of polymer used in the fiber, the diameter of the polymeric fibers, and/or the amount of bioactive compound loaded in the fiber.

For purposes of the present invention, by "implanting" or "implanted" as used herein, it is meant to be inclusive of placement of the delivery systems of the present invention into a patient to achieve systemic delivery of the bioactive compound, as well as placement of the delivery system into a patient to achieve local delivery. For example, the delivery systems of the present invention may be placed on the wound of a patient to enhance healing via release of the bioactive compound. Delivery systems may also be placed on the surface or wrapped around an organ, tissue or vessel for delivery of the bioactive compound to the organ tissue or vessel.

When used as a tissue engineering scaffold, the delivery system may be placed directly at or near the site where repair or replacement is required. For example, cartilage is an important target for tissue engineering. Millions of individuals are incapacitated by the destruction of articular cartilage by trauma or disease processes such as osteoarthritic or rheumatoid arthritis. This tissue does not repair itself. However, regeneration will occur when cells are provided a scaffold on which they can attach, migrate and synthesize their extracellular matrix. Polymeric fiber matrices coated with collagen II or a collagen II peptide comprising the D4 region have been demonstrated to promote attachment, growth and spreading of chondrocytes (presented at the First Symposium of the International Society for Matrix Biology on Jun. 14–17, 2000 and the NIH BECON Symposium, Nanoscience and Nanotechnology; Shaping Biomedical Research on Jun. 25–26, 2000). Polymeric fiber matrices of the present invention having collagen, preferably collagen II, or a collagen-like peptide, preferably the D4 period of collagen II (SEQ ID NO:1), incorporated within the fiber matrix provide even better scaffolds due to uniform distribution of the collagen or collagen-like peptide throughout the matrix.

In another embodiment of the present invention, a braided, knitted or woven structure of bioactive compound-containing fibers is prepared. These structures are prepared using an extension of the traditional 2-dimensional braiding technology in which fabric is constructed by the intertwining or orthogonal interlacing of yarns to form an integral structure through position displacement. A wide range of 3-dimensional structures comprising the bioactive compound-containing fibers can be fabricated in a circular or rectangular loom. In this embodiment, the structure may comprise only bioactive compound-containing fibers, bioactive compound-containing fibers sandwiched between polymeric fibers which contain no bioactive compound, or a mixtures of fibers containing different bioactive compounds. Like the matrix or linear assembly, this structure can be implanted into a patient for controlled release of the bioactive compound or compounds as the polymeric fibers degrade or as the bioactive compound diffuses from the polymeric fibers. Again, delivery rate of the bioactive compound can be controlled by varying the choice of polymer used in the fibers, the concentration of polymer used in the fiber, the diameter of the polymeric fibers, and/or the amount of bioactive compound loaded in the fiber.

Accordingly, the present invention also relates to methods for modulating the rate of release of a bioactive compound from a delivery system for bioactive compounds comprising a bioactive compound incorporated within or between polymeric fibers. By "modulate" or "modulating", it is meant that the rate or release of the bioactive compound incorporated within of between the polymeric fibers of the delivery system is increased or decreased. Methods for modulating the rate of release include increasing or decreasing loading of the bioactive compound incorporated within or between the polymeric fibers, selecting polymers to produce the polymeric fibers which degrade at varying rates, varying polymeric concentration of the polymeric fibers and/or varying diameter of the polymeric fibers. Varying one or more of these parameters can be performed routinely by those of skill in the art based upon teachings provided herein.

The ability of systems of the present invention to release a bioactive compound in a controlled manner was demonstrated using polymeric fiber matrices containing fluorescently labeled bovine serum albumin (FITC-BSA) dispersed between the fibers of the matrix. To construct the bioactive compound-loaded matrices, various concentrations of finely ground FITC-BSA were suspended in biodegradable polymer polylactic glycolic acid in 50:50 dimethyl formamide-:tetrahydrofuran. Suspensions contained in a glass syringe with a capillary tip were electrospun into approximately 500 nm diameter fibers via an electrostatic based self-assembly process in which a high voltage electric field was generated between the oppositely charged polymer and a metallic collection screen. At a critical voltage the charge overcomes the surface tension of the deformed polymer drop at the needle tip, producing an ultrafine jet. The similarly charged fibers are splayed and during their passage to the screen, the solvent quickly evaporates so that dry fibers accumulate randomly on the screen forming a mesh matrix.

The material properties of this mesh matrix of bioactive compound-containing fibers were examined via standard electron microscopy and tensile testing. It was found that tensile strength and the release profiles were a function of protein loading.

In vitro release of the FITC-BSA into an infinite sink of 37° C. phosphate buffered saline was also measured. This sink mimics in vivo conditions. While release in the first 24 hours after initiation was dominant, release to over 120 hours was observed with an increase in release at the point where the fibers started to breakdown.

Three dimensional matrices of the present invention comprising collagen II were also prepared via electrospinning. In these experiments, collagen was mixed with polyethylene oxide in a 1:10 ratio. Resulting fibrils had a uniform diameter of about 400 nm as determined by electron microscopy analysis of the nanofibrils. The content of collagen was 10% of the dry mass as assayed by the content of hydroxyproline. In addition, collagen was uniformly distributed as assayed by collagen-specific staining with Sirius red dye. The collagen content, as well as its uniform distribution throughout the fibers are characteristics which enhance cell attachment and growth to matrices of the present invention.

The following nonlimiting examples are provided to further illustrate the present invention.

EXAMPLES

Example 1

Preparation of Fiber Matrix Containing BSA-FITC

A 25% (w/v) solution of polylactic glycolic acid was prepared in a 50:50 mixture of dimethylformamide and tetrahydrofuran. A mixture of FITC-BSA and BSA in the ratio of 1:5 was added to the solution in order to obtain 2% protein loading. A syringe containing 5 ml of the polymer plus bioactive compound mixture was placed at an angle of 45°. The syringe was fitted with a 16 G needle with the tip of the needle at a distance of 24 cm from the metallic collection screen. A piece of nonwoven mat was placed on the metallic screen. A voltage of 20 kV was applied between the collection screen and the needle tip which resulted in fibers being sprayed into a nonwoven matrix on the metallic screen. The spraying was complete in about 4 hours.

It was found that with this specific polymer solvent system, polymer concentrations lower than 25% resulted in fibers with beads of polymers. These beads were eliminated when the polymer concentration was increased to 25% or greater. However, as will be understood by the skilled artisan upon reading this disclosure, this concentration will vary for different polymer/solvent systems and different bioactive compounds.

Example 2
In Vitro Release of Protein

In vitro release of the FITC-BSA into an infinite sink of 37° C. phosphate buffered saline was measured. Pre-weighed pieces from different regions of the mat were placed into scintillation vials and 10 ml of phosphate buffered saline were added and the capped vials were placed on a rotary shaker at 37° C. The buffer was exchanged at different points in time in order to mimic infinite sink conditions. The amount of protein released was measured in the form of fluorescence of the FITC-BSA on a spectrophotofluorometer at an excitation wavelength of 495 nm and an emission wavelength of 513 nm.

Example 3
Procollagen II DNA Cassette System cDNA cassettes were synthesized, as described in detail by Arnold et al. (Matrix Biol. 1997 16:105–16) to produce genetically engineered collagen II variants lacking consecutive fragments of 234 amino acids, defined here as D periods because of correlation with the D periodicity of collagen fibril (Piez et al. Extracellular Matrix Biochemistry. In Piez et al. Eds. New York :Elsevier; 1984 p1–40). DNA constructs were expressed in HT-1080 cells, and recombinant procollagens were purified from cell culture media, as described by Fertala et al. (Biochem J. 1994 298:31–7).

Example 4
Human Chondrocytes

Human chondrocytes were isolated from fetal epiphyseal cartilage removed under sterile conditions from femoral heads, knee condyles, and tibia plateaus. Isolated chondrocytes were cultured in a suspension in tissue culture dishes coated with poly-HEMA [poly(2-hydroxyethyl methacrylate); Polysciences, Inc., Malvern, Pa.] according to the method described by Reginato et at.(Arthritis Rheum. 1994 37:1338–49).

Example 5
Preparation of Microtiter Plates for Cell Attachment and Spreading Assays To coat microtiter plates, collagen II samples dissolved in 0.1 M acetic acid at a concentration of 50 µg/mL was added to microtiter plates and allowed to dry under a laminar flow hood overnight. The plates were then rinsed with phosphate-buffered saline (PBS) and blocked with heat-denatured bovine serum albumin (BSA; Sigma).

Example 6
Seeding of Chondrocytes on Recombinant Collagen II Variants

Human chondrocytes were cultured in a suspension in tissue culture plates coated with poly-HEMA. To isolate chondrocytes, the cell aggregates were transferred to a culture medium containing 2 mg/mL of trypsin and 2 mg/mL of collagenase. After a 2 hour incubation, released chondrocytes were passed through a 70-µm nylon filter and collected in a 50-mL conical tube. The cells were sedimented by centrifugation at 1500 rpm for 10 minutes. Then the cells were washed 5 times with Dulbecco's modified Eagle's medium (DMEM) supplemented with 10% fetal bovine serum, transferred to a fresh tissue culture dish coated with poly-HEMA, and incubated in a tissue culture incubator. After 2 hours the cells were washed with serum-free DMEM, counted, and suspended to $2 \times 10^{5^5}$ cells/mL in DMEM, 10% BSA. Fifty microliters of PBS containing 0.1 mg/mL of $MgCl_2$ and 0.1 mg/mL of $CaCl_2$ was added to each well of a microliter plate, followed by 50 µL of the cell suspension. The cells were allowed to attach to the plates for 3 hours. Microtiter plates were incubated for 3 hours, and the adhesion and the spreading of chondrocytes were evaluated.

Example 7
Attachment of Chondrocytes to the Collagen II Variants

After 3 hours of culture the cell layer was washed with PBS containing $MgCl_2$ and $CaCl_2$ and fixed by the addition of 10 µL of a 50% (w/v) glutaraldehyde solution. After 1 hour the wells were rinsed with water, and the cells were stained with a 1% solution of crystal violet in 200 mM MES [2-(N-morpholino)ethanesulfonic acid], pH 6.0, for 30 minutes at room temperature. The excess dye was washed off with water, and the cell-bound dye was dissolved with 100 µL of 10% (v/v) acetic acid. The absorbance was read at 570 nm. Results from five independent experiments were analyzed using the Cricket Graph statistical program (Cricket Software, Malvern, Pa.).

Example 8
Spreading of Chondrocytes on Recombinant Collagen II Lacking a Specific D Period To evaluate the spreading of chondrocytes seeded on collagen II with deleted D periods after 3 hours of culture, the cells were fixed by the addition of 10 µL of a 50% (w/v) glutaraldehyde solution directly to the wells and then were stained with Giemsa stain (Sigma). To determine the percentage of the spread cells, the cells' surface area was measured. Morphometric analysis of cells was done with an inverted microscope (Olympus IX5O, Olympus, Japan) equipped with a digital camera (Photometrics Systems) and connected to a personal computer. Surface areas of the chondrocytes from five nonoverlapping areas of a single well were measured using the Phase3 Imaging program (Imaging Systems). Data from five independent experiments were collected and analyzed with the Cricket Graph program.

Example 9
Synthesis of 3-dimensional Nanofibrous Matrices Containing Recombinant Collagen II Nanofibrillar matrices were synthesized using polymers with free $NH_2$ groups for the covalent binding of collagen (Zheng et al. In Vitro Cell Devel. Biol. Anim. 1998 34:679–84). Specifically, poly(L-lactic acid) ($M_w$, 200,000; Polysciences, Inc) was mixed with poly(ε-CBZ-L-lysine) ($M_w$ 260,000; Sigma) at a 4:1 ratio. The carbobenzoxy (CBZ)-protected form of L-lysine was used to prevent involvement of side chain groups in the formation of a CONH bond during peptide synthesis. A mixture of polymers was then dissolved in chloroform and used to generate nanofibrillar material in the electrostatic spinning process. In this nonmechanical technique a high electric field is generated between a polymer fluid contained in a glass syringe with a capillary tip and a metallic collection screen. When the voltage reaches a critical value, the charge overcomes the surface tension of the deformed drop of the suspended polymer solution created on the capillary tip, producing a jet. The electrically charged jet undergoes a series of electrically induced bending instabilities during its passage to the collection screen, hyperstretching the jet. This process is accompanied by the rapid evaporation of the solvent. The dry fibers are accumulated on the surface of the collection screen, resulting in a nonwoven mesh of nanofibers. The covalent binding of the collagen was done according to the method developed by Zheng et al, supra. To activate CBZ-protected $\epsilon$-amino groups, the matrices were placed in a 4.5M HCl solution in glacial acetic acid and incubated for 30 minutes at 37° C. The samples were neutralized by the addition of 0.1M sodium carbonate and then stored in sterile water at 4° C. Recombinant collagen stock solutions were diluted to a final concentration of 200 $\mu$g/mL with 10 mM of MOPS [3-(N-Morpholino) propanesulfonic acid], adjusted to pH 4.5, containing 5 mg/mL of water-soluble carbodiimide [1-ethyl-3-(3-bimethylaminopropyl) carbodiimide; Pierce]. The activated amino groups were permitted to react with collagen for 48 h at 4° C. Unbound collagen was then removed by washing of the matrices with 10 mM of HCl, followed by a washing with water. The efficiency of incorporation of collagen into nanofibrous matrices was determined by an analysis of the hydroxyproline content after acid hydrolysis and reaction with p-dimethylaminobenzaldehyde.

Example 10

Growth of Chondrocytes in a 3-dimensional Nanofibrous Scaffold

The nanofibrous scaffolds coated with collagen II variants were placed into separate wells of a microtiter plate. Chondrocytes were seeded onto the scaffolds in the amount of 10,000 cells/well and cultured for up to 50 days. Fifty percent of the media supplemented with 40 $\mu$g/mL of ascorbic acid was changed every 48 hours. After 48 hours of culture the cells seeded onto nanofibrillar matrices were examined by scanning electron microscopy. In addition, after 50 days, the morphology of the synthesized matrix was examined by light microscopy, and the substructure of the synthesized extracellular matrix was examined by transmission electron microscopy.

Example 11

Analysis of Secretion of Collagen II and Collagen IX

Proteins secreted into the media by chondrocytes cultured for 50 days in matrices coated with full-length collagen II were precipitated with polyethylene glycol (8,000 $M_w$; Sigma) at a concentration of 5% (w/v). The proteins were then collected by centrifugation at 13,000×g for 30 minutes at 4° C., dissolved in 0.1M Tris-HCl buffer (pH 7.4) containing 0.4M NaCl, 25 mM EDTA, and 0.04% $NaN_3$. Then collagens II and IX were examined by SDS-polyacrylamide gel electrophoresis under reducing conditions, followed by electroblotting and Western analysis with anticollagen type-specific antibodies (Chemicon, Inc.).

What is claimed is:

1. A tissue engineering scaffold comprising collagen or a collagen-like peptide incorporated within polymeric fiber matrix.

2. The tissue engineering scaffold of claim 1 wherein the collagen is collagen II.

3. The tissue engineering scaffold of claim 1 wherein the collagen-like peptide comprises amino acids 703 to 936 of collagen II.

4. A tissue engineering scaffold comprising a collagen-like peptide consisting of SEQ ID NO:1.

* * * * *